United States Patent
Glass

(10) Patent No.: US 7,122,648 B2
(45) Date of Patent: Oct. 17, 2006

(54) ION CHANNEL RECEPTOR AND USES THEREOF

(75) Inventor: David J. Glass, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 607 days.

(21) Appl. No.: 10/622,896

(22) Filed: Jul. 18, 2003

(65) Prior Publication Data

US 2004/0018547 A1    Jan. 29, 2004

Related U.S. Application Data

(60) Provisional application No. 60/397,290, filed on Jul. 19, 2002.

(51) Int. Cl.
*C07H 21/04* (2006.01)
*C07K 14/00* (2006.01)

(52) U.S. Cl. ............... 536/23.1; 536/23.5; 530/350

(58) Field of Classification Search ............ None
See application file for complete search history.

(56) References Cited

OTHER PUBLICATIONS

Bodine, et al, (2001) Science 294: 1704-1708.
Bodine, et al. 2001 Nature Cell Biology 3:1014-1019.
Rommel, et al (1999) Science 286: 1738-1741.
Coleman, et al. (1995) The Journal of Biological Chemistry 270: 12109-12116.
Rommel, et al. Nature (2001) 3: 1009-1013.

*Primary Examiner*—Eileeen B. O'Hara
*Assistant Examiner*—Sandra Wegert
(74) *Attorney, Agent, or Firm*—Valeta Gregg, Esq.

(57) ABSTRACT

The present invention provides for nucleic acid sequences that encode novel mammalian intracellular signaling polypeptides, designated MINC102. The invention also provides assay systems that may be used to detect and/or measure agents that bind the MINC102 gene product. The present invention also provides for diagnostic and therapeutic methods for treating muscle atrophy by inhibiting expression or activity of MINC102.

2 Claims, No Drawings

SEQUENCE LISTING

<160> NUMBER OF SEQ ID NOS: 4

<210> SEQ ID NO 1
<211> LENGTH: 1837
<212> TYPE: DNA
<213> ORGANISM: human

<400> SEQUENCE: 1

```
gactcactat agggcggccg cgaattcggc accagcacca ccggagtggg ctccgtgggt      60
gctggggcag gagtttcctc actccccgcc tggccgtcgc tcctccgctg actccgcgcc     120
cttctacggg ccgtctccca ccctctgagc ggacgcaggg agtcgatgcc gggcgaaccg     180
ggcgccatga agggcagctg cctaacgggc gccgcggcg agggggctggc cggctgaggg     240 cccgcgctgg gccgaggcat gcggagcccg ggcgggatcc tgctccaggc gctgccccgg     300
ctgctgcagc acgccgccct cccgggcctc gccgagctgc cggcccgctg ggccctgccg     360
cggggtgcgg gcggggacgg cccggcggac cgccttcccc gcggggcgg ggcgagcgcg     420 gcggcggcag cagcggcggc ctcgggcgcc ctgctcggcg cctatctgga gcgccacggt     480
ccgcccgagg cttcggagct gccggagccg ggcggggcct tggcgggcgg ccccgggagt     540
ggcggcggcg gcgtggtggt cggcgtggct gaggtgagaa actggcgctg ctgctgcctc     600
ggcagcacct gttggtgccg gagcctcgtg ctggtctgcg tgttggccgc cctgtgcttc     660
gcttccctgg ccctggtccg ccgctacctt caccacctcc tgctgtgggt ggagagcctt     720
gactcgctgc tgggggtcct gctcttcgtc gtgggcttca tcgtggtctc tttcccctgc     780
ggctggggct acatcgtgct caacgtggcc gctggctacc tgtacggctt cgtgctgggc     840
atgggtctga tgatggtggg cgtcctcatc ggcaccttca tcgcccatgt ggtctgcaag     900
cggctcctca ccgcctgggt ggccgccagg atccagagca gcgagaagct gagcgcggtt     960
attcgcgtag tggaggagg aagcggcctg aaagtggtgg cgctggccag actgacaccc    1020
ataccttttg ggcttcagaa tgcagtgttt tcgattactg atctctcatt acccaactat    1080
ctgatggcat cttcggttgg actgcttcct acccagcttc tgaattctta cttgggtacc    1140
accctgcgga caatggaaga tgtcattgca gaacagagtg ttagtggata ttttgttttt    1200
tgtttacaga ttattataag tataggcctc atgttttatg tagttcatcg agctcaagtg    1260
gaattgaatg cagctattgt agcttgtgaa atggaactga aatcttctct ggttaaaggc    1320
```

-continued

```
aatcaaccaa ataccagtgg ctcttcattc tacaacaaga ggaccctaac attttctgga    1380
ggtggaatca atgttgtatg attctaatga gatacgtgat tgtcaagagc ctagtgtgct    1440
atctaaggtc tagcagtcac ttcactagtg ggcagagaca agttctaatt gtattacagc    1500
acaaacaaaa ctgactagtt tttaaattgc acaattttt tttttttaaag caagaatcat    1560 tttctgggta tgtaagtgta aatgtagatg caaatttggc tgcacctctt tatcatgcct    1620
gtattggcct ataggtctgc actttagtgt tttttaattg ttttatttct gtgtatttac    1680
gaacagagaa ataacccaaa tattatttct gcttagtgtc tttatttata aagcccatga    1740
gtagtttgta tgcatctttc ctacttgtaa agatgagtaa aagtatgcag ttttaaattt    1800
ataatattat tggatgttct ttgctttggt agtcttt                             1837
```

<210> SEQ ID NO 2
<211> LENGTH: 376
<212> TYPE: PRT
<213> ORGANISM: human

<400> SEQUENCE: 2

```
Met Arg Ser Pro Gly Gly Ile Leu Leu Gln Ala Leu Pro Arg Leu Leu
  1               5                  10                  15

Gln His Ala Ala Leu Pro Gly Leu Ala Glu Leu Pro Ala Arg Trp Ala
             20                  25                  30

Leu Pro Arg Gly Ala Gly Gly Asp Gly Pro Ala Asp Arg Leu Pro Arg
         35                  40                  45

Gly Gly Gly Ala Ser Ala Ala Ala Ala Ala Ala Ala Ser Gly Ala
     50                  55                  60

Leu Leu Gly Ala Tyr Leu Glu Arg His Gly Pro Pro Glu Ala Ser Glu
 65                  70                  75                  80

Leu Pro Glu Pro Gly Gly Ala Gly Gly Pro Ser Gly Gly Gly
                 85                  90                  95

Val Val Val Gly Val Ala Glu Val Arg Asn Trp Arg Cys Cys Cys Leu
                100                 105                 110

Gly Ser Thr Cys Trp Cys Arg Ser Leu Val Leu Cys Val Leu Ala
                115                 120                 125

Ala Leu Cys Phe Ala Ser Leu Ala Leu Val Arg Arg Tyr Leu His His
            130                 135                 140

Leu Leu Leu Trp Val Glu Ser Leu Asp Ser Leu Leu Gly Val Leu Leu
145                 150                 155                 160

Phe Val Val Gly Phe Ile Val Val Ser Phe Pro Cys Gly Trp Gly Tyr
                165                 170                 175

Ile Val Leu Asn Val Ala Ala Gly Tyr Leu Tyr Gly Phe Val Leu Gly
                180                 185                 190

Met Gly Leu Met Met Val Gly Val Leu Ile Gly Thr Phe Ile Ala His
                195                 200                 205

Val Val Cys Lys Arg Leu Leu Thr Ala Trp Val Ala Ala Arg Ile Gln
            210                 215                 220

Ser Ser Glu Lys Leu Ser Ala Val Ile Arg Val Glu Gly Gly Ser
225                 230                 235                 240

Gly Leu Lys Val Val Ala Arg Leu Thr Pro Ile Pro Phe Gly Leu Gln
                245                 250                 255

Asn Ala Val Phe Ser Ile Thr Asp Leu Ser Leu Pro Asn Tyr Leu Met
                260                 265                 270

Ala Ser Ser Val Gly Leu Leu Pro Thr Gln Leu Leu Asn Ser Tyr Leu
```

-continued

```
                275                 280                 285
Gly Thr Thr Leu Arg Thr Met Glu Asp Val Ile Ala Glu Gln Ser Val
            290                 295                 300

Ser Gly Tyr Phe Val Phe Cys Leu Gln Ile Ile Ser Ile Gly Leu
305                 310                 315                 320

Met Phe Tyr Val Val His Arg Ala Gln Val Glu Leu Asn Ala Ala Ile
                325                 330                 335

Val Ala Cys Glu Met Glu Leu Lys Ser Ser Leu Val Lys Gly Asn Gln
            340                 345                 350

Pro Asn Thr Ser Gly Ser Phe Tyr Asn Lys Arg Thr Leu Thr Phe
        355                 360                 365

Ser Gly Gly Ile Asn Val Val
    370                 375
```

<210> SEQ ID NO 3
<211> LENGTH: 1143
<212> TYPE: DNA
<213> ORGANISM: mouse

<400> SEQUENCE: 3

| | | | | | |
|---|---|---|---|---|---|
| atgcggaacc | ccggtgggag | cctgccccac | acgctgcccc | gggccttgca | gcacgccggt | 60 |
| cggacgggag | tcgtggagca | gccgggccgc | tgggcaccgg | agcggacagc | gggaggggac | 120 |
| cgctcggagg | accgccttcc | ccgcggggc | ggggccagcg | cggcggcggc | tgctgctgcg | 180 |
| gcggcggcct | cggcgccct | gctcggcgcc | tatctggagc | gccacggtct | gcccgcggcc | 240 |
| tcggacttgc | cggcgccggc | cggggcgttg | gcaggcggcc | ccgggagcgg | cggcggcgtg | 300 |
| gtggtcgggg | tggccgaggt | gagaaactgg | cgctgctgct | gcctcggcag | cacctgttgg | 360 |
| tgccggagcc | tcgtgctggt | gtgcgtgctg | gccgccctgt | gcttcgcttc | cctggccctg | 420 |
| gtccgccgct | acctgcagca | cctcctgctc | tgggtggaga | gcctcgactc | gctgctcggt | 480 |
| gtcctgctct | tcgtcgtggg | cttcatcgtg | gtctccttcc | cctgcggttg | gggctacatc | 540 |
| gtgcttaatg | tggcggccgg | ctacctgtac | ggcttcgtgc | taggcatggg | gctcatggtg | 600 |
| gtgggcgtcc | tcattggcac | ctttatcgct | catgtggtct | gcaagcggct | actcaccgcc | 660 |
| tgggtggctg | ccaggatcca | gaacagcgac | aagctgagcg | ccgttatccg | cgtcgtggag | 720 |
| ggaggaagcg | gcctgaaggt | ggtggcgctg | gcccggctga | ctcccatacc | ttttgggctt | 780 |
| cagaatgcag | tgttttcgat | tactgacgtc | cccttgccca | gctacctgat | ggcgtcttca | 840 |
| gctgggctgc | tcccgactca | gcttctgaat | tcttacttgg | gaaccacact | acggactatg | 900 |
| gaagatgtca | tcgcagaaca | aagtcttagt | ggctattttg | tcttttgttt | acagattgtt | 960 |
| ataagcattg | gcctcatgtt | ttatgtagtc | catcgcgctc | aagtggaatt | gaatgcagct | 1020 |
| attgtagctt | gtgagatgga | actgaaaacc | tctctggtta | aaggcaatca | atcggatccc | 1080 |
| agtggctctt | ccttctacaa | caagaggacc | ctcacgtttt | ctggaggtgg | aatcaatatt | 1140 |
| gta | | | | | | 1143 |

<210> SEQ ID NO 4
<211> LENGTH: 381
<212> TYPE: PRT
<213> ORGANISM: mouse

<400> SEQUENCE: 4

```
Met Arg Asn Pro Gly Gly Ser Leu Pro His Thr Leu Pro Arg Ala Leu
1               5                   10                  15
```

-continued

```
Gln His Ala Gly Arg Thr Gly Val Val Glu Gln Pro Gly Arg Trp Ala
             20                  25                  30

Pro Glu Arg Thr Ala Gly Gly Asp Arg Ser Glu Asp Arg Leu Pro Arg
             35                  40                  45

Gly Gly Gly Ala Ser Ala Ala Ala Ala Ala Ala Ala Ala Ala Ala Ser
 50                  55                  60

Gly Ala Leu Leu Gly Ala Tyr Leu Glu Arg His Gly Leu Pro Ala Ala
 65                  70                  75                  80

Ser Asp Leu Pro Ala Pro Ala Gly Ala Leu Ala Gly Gly Pro Gly Ser
             85                  90                  95

Gly Gly Gly Val Val Val Gly Val Ala Glu Val Arg Asn Trp Arg Cys
            100                 105                 110

Cys Cys Leu Gly Ser Thr Cys Trp Cys Arg Ser Leu Val Leu Val Cys
            115                 120                 125

Val Leu Ala Ala Leu Cys Phe Ala Ser Leu Ala Leu Val Arg Arg Tyr
    130                 135                 140

Leu Gln His Leu Leu Trp Val Glu Ser Leu Asp Ser Leu Leu Gly
145                 150                 155                 160

Val Leu Leu Phe Val Val Gly Phe Ile Val Val Ser Phe Pro Cys Gly
                    165                 170                 175

Trp Gly Tyr Ile Val Leu Asn Val Ala Ala Gly Tyr Leu Tyr Gly Phe
                180                 185                 190

Val Leu Gly Met Gly Leu Met Val Gly Val Leu Ile Gly Thr Phe
            195                 200                 205

Ile Ala His Val Val Cys Lys Arg Leu Leu Thr Ala Trp Val Ala Ala
            210                 215                 220

Arg Ile Gln Asn Ser Asp Lys Leu Ser Ala Val Ile Arg Val Val Glu
225                 230                 235                 240

Gly Gly Ser Gly Leu Lys Val Val Ala Leu Ala Arg Leu Thr Pro Ile
                245                 250                 255

Pro Phe Gly Leu Gln Asn Ala Val Phe Ser Ile Thr Asp Val Pro Leu
                260                 265                 270

Pro Ser Tyr Leu Met Ala Ser Ser Ala Gly Leu Leu Pro Thr Gln Leu
            275                 280                 285

Leu Asn Ser Tyr Leu Gly Thr Thr Leu Arg Thr Met Glu Asp Val Ile
290                 295                 300

Ala Glu Gln Ser Leu Ser Gly Tyr Phe Val Phe Cys Leu Gln Ile Val
305                 310                 315                 320

Ile Ser Ile Gly Leu Met Phe Tyr Val Val His Arg Ala Gln Val Glu
                325                 330                 335

Leu Asn Ala Ala Ile Val Ala Cys Glu Met Glu Leu Lys Thr Ser Leu
            340                 345                 350

Val Lys Gly Asn Gln Ser Asp Pro Ser Gly Ser Ser Phe Tyr Asn Lys
            355                 360                 365

Arg Thr Leu Thr Phe Ser Gly Gly Ile Asn Ile Val
            370                 375                 380
```

ION CHANNEL RECEPTOR AND USES THEREOF

STATEMENT OF RELATED PATENT APPLICATIONS

This application claims benefit under 35 USC § 119(e) of U.S. Provisional Application No. 60/397,290, filed Jul. 19, 2002, which application is herein specifically incorporated by reference in its entirety into this application.

FIELD OF THE INVENTION

The present invention relates to a muscle ion channel receptor, MINC102, and uses thereof in methods for prevention of muscle atrophy.

BACKGROUND OF THE INVENTION

A decrease in muscle mass, or atrophy, is associated with various physiological and pathological states. For example, muscle atrophy can result from denervation due to nerve trauma; degenerative, metabolic or inflammatory neuropathy, e.g. Guillian-Barré syndrome; peripheral neuropathy; or nerve damage caused by environmental toxins or drugs; from denervation due to a motor neuropathy including, for example, adult motor neuron disease, such as Amyotrophic Lateral Sclerosis (ALS or Lou Gehrig's disease); infantile and juvenile spinal muscular atrophies; autoimmune motor neuropathy with multifocal conductor block. Muscle atrophy may also result from chronic disease resulting from, for example, paralysis due to stroke or spinal cord injury; skeletal immobilization due to trauma, such as, for example, fracture, sprain or dislocation; or prolonged bed rest. Metabolic stress or nutritional insufficiency, which may also result in muscle atrophy, include inter alia the cachexia of cancer, AIDS, and other chronic illnesses, fasting or rhabdomyolysis, and endocrine disorders such as disorders of the thyroid gland and diabetes. Muscle atrophy may also be due to a muscular dystrophy syndrome such as Duchenne, Becker, myotonic, fascioscapulohumeral, Emery-Dreifuss, oculopharyngeal, scapulohumeral, limb girdle, and congenital types, as well as the dystrophy known as Hereditary Distal Myopathy. Muscle atrophy may also be due to a congenital myopathy, such as benign congenital hypotonia, central core disease, nemalene myopathy, and myotubular (centronuclear) myopathy.

Insulin-like growth factor 1 (IGF-1), is a small protein growth factor that has been shown to cause hypertrophy when expressed in skeletal muscle (Coleman et al. (1995) J. Biol. Chem. 270:12109-16). A signaling pathway activated in response to IGF-1 is the phosphatidylinositol 3-kinase (PI3K)/Akt pathway (PI3K/Akt). (Vanhaesebroeck et al. (1997) TIBS 22:267). PI3K causes phosphorylation of the cell membrane-bound molecule phosphatidylinositol 4,5-bisphosphate at the 3 position, resulting in phosphatidylinositol 3,4,5-trisphosphate. Akt then translocates to the cell membrane and binds to phosphatidylinositol 3,4,5-trisphosphate, where the Akt is activated.

BRIEF SUMMARY OF THE INVENTION

This invention is based in part on the discovery that expression of a novel mammalian intracellular signaling protein, designated MINC102, is increased in the presence of muscle atrophy or conditions which promote muscle atrophy. Accordingly, this discovery provides a new therapeutic target for inhibition, reduction, or prevention of muscle atrophy, as well as a marker of the development and progression of muscle atrophy.

In a first aspect, the invention features an isolated nucleic acid sequence encoding a human MINC102. In a specific embodiment, the nucleic acid sequence encodes human MINC102 comprising the sequence of SEQ ID NO:1; a nucleotide sequence which, but for the degeneracy of the genetic code, would hybridize to the complement of SEQ ID NO:1, and which encodes a molecule having the biological activity of MINC102; or a nucleotide sequence whose complement hybridizes under stringent conditions to the sequence of SEQ ID NO:1 and encodes a protein having MINC102 activity, wherein the stringent conditions are 30% formamide in 5×SSPE (0.18 M NaCl, 0.01 M NaPO$_4$, pH 7.7, 0.001 M EDTA) buffer at a temperature of 42° C. and remaining bound when washed at 42° C. with 0.2×SSPE.

In a second aspect, the invention features a human MINC102 protein encoded by the nucleic acid sequence of SEQ ID NO:1; a nucleotide sequence which, but for the degeneracy of the genetic code, would hybridize to the complement of SEQ ID NO:1, and which encodes a molecule having the biological activity of MINC102; or a nucleotide sequence whose complement hybridizes under stringent conditions to the sequence of SEQ ID NO:1 and encodes a protein having MINC102 activity. In a specific embodiment, the human MINC102 protein comprises the amino acid sequence of SEQ ID NO:2, or biologically active fragments thereof. In addition, the invention encompasses allelic variants of SEQ ID NO:2, as well as insertional, deletional, and/or substitutional variants thereof which substantially retain the functional characteristics of MINC102. Further, the invention encompasses a protein having amino acid sequences at least 95%, at least 97%, or at least 98% homologous to SEQ ID NO:2.

In a third aspect, the invention features an isolated nucleic acid sequence encoding a mouse MINC102 comprising SEQ ID NO:3; a nucleotide sequence which, but for the degeneracy of the genetic code, would hybridize to the complement of SEQ ID NO:3, and which encodes a molecule having the biological activity of MINC102; or a nucleotide sequence whose complement hybridizes under stringent conditions to the sequence of SEQ ID NO:3 and encodes a protein having MINC102 activity.

In a fourth aspect, the invention features a mouse MINC102 protein comprising SEQ ID NO:4, or biologically active fragments thereof, as well as allelic, insertional, deletional, and/or substitutional variants thereof which substantially retain the functional characteristics of MINC102.

In a fifth aspect, the invention features vectors comprising the nucleic acid molecules of the invention, including expression vectors comprising a the nucleic acid molecules operatively linked to an expression control sequence. The invention further encompasses host-vector systems for the production of a fusion polypeptide which comprise the expression vector, in a suitable host cell; host-vector systems wherein the suitable host cell is a bacterial, yeast, insect, mammalian cell; an E. coli cell, or a COS or CHO cell.

In a sixth aspect, the invention features a method of producing a MINC102 protein of the invention, comprising culturing a host cell transfected with a vector comprising a nucleic acid sequence of the invention, under conditions suitable for expression of the protein from the host cell, and recovering the protein so produced.

In a seventh aspect, the invention features screening methods for identifying agents capable of binding a MINC102 protein of the invention. More specifically, the invention provides methods of identifying agents capable of modulating (e.g., enhancing or inhibiting) human MINC102 activity. Agents capable of inhibiting MINC102 are valuable as potential therapeutics for the treatment of muscle atrophy or a disease or condition associated with muscle atrophy.

In an eighth aspect, the invention features a method of treating, inhibiting and/or reducing muscle atrophy, comprising administering an effective amount of an agent capable of inhibiting MINC102 expression or activity. In one embodiment, the inhibitor is an agent capable of inhibiting MINC102 expression. More specifically, the agent capable of inhibiting MINC102 expression is an antisense molecule, a ribozyme or triple helix, or a short interfering RNA (siRNA) capable of silencing MINC102 gene expression. In another embodiment, the inhibitor is an agent capable of inhibiting MINC102 activity. More specifically, the agent capable of inhibiting MINC102 activity is a MINC102 antagonist, including an antibody specific for MINC102. The antibody may be polyclonal, monoclonal, chimeric, humanized, or a wholly human antibody. In another specific example, the agent capable of inhibiting MINC102 activity is an activator of the Akt pathway, such as insulin-like growth factor 1 (IGF-1), clenbuterol, albuterol, or salbuterol.

In a ninth aspect, the invention features pharmaceutical compositions comprising a MINC102 inhibitor useful for treatment of muscle atrophy. In one embodiment, the pharmaceutical composition comprises an agent identified by a screening method of the invention. In another embodiment, the agent is an agent capable of inhibiting MINC102 expression or activity.

In a tenth aspect, the invention features a non-human transgenic animal comprising a modification of an endogenous MINC102 gene. As described more fully in co-pending U.S. Ser. No. 09/732,234 filed Dec. 7, 2000, the transgenic animal of the invention is generated by targeting the endogenous MINC102 gene with a large targeting vector (LTVEC). In one embodiment of the transgenic animal of the invention, the animal is a knock-out wherein the MINC102 gene is altered or deleted such that the function of the endogenous MINC102 protein is reduced or ablated. In another embodiment, the transgenic animal is a knock-in animal modified to comprise an exogenous human MINC102 gene. Such transgenic animals are also useful in identifying agents that treat muscle atrophy and related disorders mediated by the human MINC102 protein.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

By the term "MINC102" protein is meant a protein having the sequence of SEQ ID NO:2 (human) or SEQ ID NO:4 (mouse), or a functional equivalent thereof. By the term a "functional equivalent of MINC102" is meant a protein that substantially has the function or the activity of MINC102, and has at least 90%, preferably at least 95%, most preferably at least 99% homology in the nucleotide sequence encoding the protein or the amino acid sequence, when optimally aligned with the original MINC102 protein. Such a functional equivalent of MINC102 includes substitution, addition, deletion or insertion of at least one nucleotide, in addition to the original sequence in the terminal inverted repeat sequence or the open reading frame that is a functional site, and has at least functions or activities substantially equivalent to those of the original MINC102 protein. Such a functional equivalents may include substitution of at least one amino acid (preferably conservative substitution), or additional amino acid (e.g., a leader sequence, a secretion sequence, and/or a sequence that would advantageously function in purification), in addition to the original sequence. It is appreciated that production of these functional equivalents is within a scope of technical knowledge that can be routinely obtained by those skilled in the art.

By the term "MINC102-mediated condition" is meant a disease or condition associated with, or modified by, activity and/or expression of the MINC102 protein. For example, the applicants have shown that the expression of MINC102 is increased during the process of muscle atrophy, and the upregulation of MINC102 is not seen under conditions which promote muscle growth or hypertrophy.

By the term "inhibitor" is meant a substance that retards or prevents an event, such as a MINC102 expression or activity. Common inhibitors include but are not limited to antisense molecules, siRNA molecules, antibodies and antagonists capable of activating the Akt pathway, such as IGF1-1 or clenbuterol.

General Description

This invention is based in part on the observation that the expression of the muscle specific ion channel MINC102 is increased under conditions of muscle atrophy. This relationship has been verified in a number of atrophy models. Accordingly, this observation provides a new therapeutic approach to the treatment of muscle atrophy by inhibiting the expression or activity of MINC102.

Protein and Nucleic Acid Sequence

The present invention includes the nucleic acid sequence of SEQ ID NOs:1 and 3, as well as nucleotide sequences that hybridizes under stringent conditions to the complement of the nucleotide sequence of SEQ ID NO:1 and which encodes human or murine MINC102, wherein said stringent conditions are 30% formamide in 5×SSPE (0.18 M NaCl, 0.01 M NaPO$_4$, pH 7.7, 0.001 M EDTA) buffer at a temperature of 42° C. and remaining bound when subject to washing at 42° C. with 0.2×SSPE; and nucleotide sequences which, as a result of the degeneracy of the genetic code, differs from the nucleic acid of SEQ ID NO:1 or sequences which hybridize thereto and which encode human MINC102 (SEQ ID NO:2) or murine MINC102 (SEQ ID NO:4). Further encompassed by the invention are nucleic acids encoding a protein having 90%, 95%, or 99% identify to the protein of SEQ ID NO:2. The similarity between different molecules can be expressed by the degree of homology between the nucleic acid or protein sequences. 50% homology means, for example, that 50 out of 100 nucleotides or amino acid positions in the sequences correspond to each other. The homology of proteins is determined by sequence analysis. Homologous DNA sequences can also be identified by the hybridization technique.

In addition, the invention contemplates vectors that comprise MINC102 encoding sequences, wherein the nucleic acid molecule is operatively linked to an expression control sequence capable of directing its expression in a host cell. The invention further contemplates host-vector systems for the production of MINC102, including bacterial, yeast, insect, amphibian or mammalian cells.

In specific embodiments, the invention provides for nucleotide fragments of the nucleic sequences encoding MINC102. Such fragments may consist of at least 8 nucleotides of an MINC102 gene sequence; in other embodiments, the nucleic acids consists of at least 25 continuous nucleotides, 50 nucleotides, 100 nucleotides, 150 nucleotides, 150 nucleotides, or 200 nucleotides of a MINC102. In another embodiment the nucleic acids are smaller than 47 nucleotides in length. Such fragments may be used as probes or otherwise and should consist of a sufficient number of nucleotides such that the fragment will hybridize to the MINC102 gene. The hybridization should be discriminating in that such fragments are useful as a marker of atrophy, by for example detecting changes in the expression levels of MINC102. The invention also relates to nucleic acids hybridizable or complementary to the foregoing sequences. All sequences may be single or double stranded. In addition, the nucleotide sequences of the invention may include nucleotide sequences that encode polypeptides having at least 80%, 85%, 90%, 95%, 98%, or higher amino acid sequence identity to the polypeptides encoded by SEQ ID NOs:1 and 3.

Screening Assays

The present invention provides methods for identifying agents (e.g., candidate compounds or test compounds) that are capable of inhibiting MINC102-mediated activity or expression. Agents identified through the screening method of the invention are potential therapeutics for use in the treatment of muscle atrophy and related conditions.

Examples of agents to be tested by the screening methods of the invention include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art. Test compounds further include, for example, antibodies (e.g., polyclonal, monoclonal, humanized, anti-idiotypic, chimeric, and single chain antibodies as well as Fab, F(ab').sub.2, Fab expression library fragments, and epitope-binding fragments of antibodies). Further, agents or libraries of compounds may be presented, for example, in solution, on beads, chips, bacteria, spores, plasmids or phage.

In one embodiment, agents that bind MINC102 are identified in a cell-based assay system. In accordance with this embodiment, cells expressing a MINC102 protein or protein fragment are contacted with a candidate (or a control compound), and the ability of the candidate compound to bind MINC102 is determined. In one embodiment, the ability of a test compound to bind to MINC102 may be determined by a competitive binding assay, for example, by obtaining cells expressing MINC102, contacting the cells with one agent known to bind to MINC102 and a second agent whose ability to bind MINC102 is unknown, detecting the amount of binding of the first agent alone and comparing that amount with the amount of binding of the first agent in the presence of the second agent. Binding of a compound to MINC102 may be determined in a number of ways known to the art, including for example, radioactive detection, fluorescence detection, chromogenic detection, mass spectroscopy, and plasmon resonance, or by detection of a biological response through measurement of $Ca^{2+}$ ion flux, cAMP, $IP_3$, $PIP_3$ and transcription of reporter genes.

A cell-based assay may be used to identify a test agent that inhibits muscle atrophy, comprising (a) obtaining cells that express (i) MINC102, (ii) a MINC102 substrate/reporter construct capable of measuring MINC102 substrate activation; (b) subjecting the cells to a test agent; (c) measuring the amount of MINC102 substrate activation in (a), wherein an agent capable of reducing activation of the MINC102 substrate is used to identify a test agent that inhibits atrophy in muscle cells. Changes in MINC102 activity may be measured by PCR, Taqman PCR, phage display systems, gel electrophoresis, yeast-two hybrid assay, Northern or Western analysis, immunohistochemistry, a conventional scintillation camera, a gamma camera, a rectilinear scanner, a PET scanner, a SPECT scanner, a MRI scanner, a NMR scanner, or an X-ray machine. The change in MINC102 protein activity may be detected by detecting a change in the interaction of MINC102 with one or more proteins or by detecting a change in the level of one or more of the proteins in the MINC102 pathway.

The cell is preferably a mammalian skeletal muscle cell isolated from an animal, including primary or established cultures of such cells, as well as tissue containing skeletal cells. In preferred embodiments of the method the cells are fibroblasts, muscle cells, myoblasts, or C2C12 cells. Further, the cells may express a MINC102 protein or protein fragment endogenously or be genetically engineered to express a MINC102 protein or protein fragment. To identify ligands of MINC102, cells expressing the receptor may be screened against a panel of know peptides utilizing binding assay. In these binding assays, the peptide to be tested is labeled. Cells expressing the MINC102 are then incubated with labeled test compounds, in binding buffer, in cell culture dishes. To determine non-specific binding, unlabeled peptide may be added to the wells. After the incubation, bound and free peptides are separated and detection activity measured in each well.

The ability of the candidate compound to alter the activity of MINC102 can be determined by methods known to those of skill in the art, for example, by flow cytometry, a scintillation assay, immunoprecipitation or western blot analysis. For example, modulators of MINC102-mediated activity may be identified using a biological readout in cells expressing a MINC102 protein or protein fragment. Antagonists are identified by incubating cells or cell fragments expressing MINC102 with test compound and measuring a biological response in these cells and in parallel cells or cell fragments not expressing MINC102. An increased biological response in the cells or cell fragments expressing MINC102 compared to the parallel cells or cell fragments indicates the presence of an agonist in the test sample, whereas a decreased biological response indicates an antagonist.

Detection of binding and/or modulation of a test agent to a MINC102 protein may be accomplished by detecting a biological response, such as, for example, measuring $Ca^{2+}$ ion flux, cAMP, $IP_3$, $PIP_3$ or transcription of reporter genes. Suitable reporter genes include endogenous genes as well as exogenous genes that are introduced into a cell by any of the standard methods familiar to the skilled artisan, such as transfection, electroporation, lipofection and viral infection.

In another embodiment, agents that bind MINC102 are identified in a cell-free assay system. In accordance with this embodiment, a MINC102 protein or protein fragment is contacted with a test (or control) compound and the ability of the test compound to bind MINC102 is determined. In vitro binding assays employ a mixture of components including a MINC102 protein or protein fragment, which may be part of a fusion product with another peptide or polypeptide, e.g., a tag for detection or anchoring, and a sample suspected of containing a natural MINC102 binding target. A variety of other reagents such as salts, buffers, neutral proteins, e.g., albumin, detergents, protease inhibitors, nuclease inhibitors, and antimicrobial agents, may also be included. The mixture components can be added in any order that provides for the requisite bindings and incubations may be performed at any temperature that facilitates optimal binding. The mixture is incubated under conditions whereby the MINC102 protein binds the test compound. Incubation periods are chosen for optimal binding but are also minimized to facilitate rapid, high-throughput screening.

After incubation, the binding between the MINC102 protein or protein fragment and the suspected binding target is detected by any convenient way. When a separation step is useful to separate bound from unbound components, separation may be effected by, for example, precipitation or immobilization, followed by washing by, e.g., membrane filtration or gel chromatography. One of the assay components may be labeled which provides for direct detection such as, for example, radioactivity, luminescence, optical or electron density, or indirect detection such as an epitope tag or an enzyme. A variety of methods may be used to detect the label depending on the nature of the label and other assay components, e.g., through optical or electron density, radioactive emissions, nonradiative energy transfers, or indirectly detected with antibody conjugates.

It may be desirable to immobilize either the receptor protein or fragment to facilitate separation of complexes from uncomplexed forms of one of the proteins, as well as to accommodate automation of the assay. Techniques for immobilizing proteins on matrices can be used in the drug screening assays. In one embodiment, a fusion protein is provided which adds a domain that allows the protein to be bound to a matrix.

In another embodiment, agents that inhibit MINC102-mediated activity or expression are identified in an animal model. Examples of suitable animals include, but are not limited to, mice, rats, rabbits, monkeys, guinea pigs, dogs and cats. In accordance with this embodiment, the test compound or a control compound is administered (e.g., orally, rectally or parenterally such as intraperitoneally or intravenously) to a suitable animal and the effect on the MINC102-mediated activity or expression is determined. Specifically, this method may be used to identify an agent capable of inhibiting the development and/or progression of muscle atrophy, and related conditions.

Antibodies to Human MINC102

The present invention provides for an antibody that specifically binds human MINC102 and is useful for treating a MINC102-mediated activity such as muscle atrophy. According to the invention, a MINC102 protein, protein fragment, derivative or variant, may be used as an immunogen to generate immunospecific antibodies. Such immunogens can be isolated by any convenient means, including the methods described above. Antibodies may be blocking antibodies or activating antibodies and include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

For preparation of polyclonal or monoclonal antibodies directed toward MINC102 polypeptides, any technique which provides for the production of antibody molecules by continuous cell lines in culture may be used. For example, the hybridoma technique originally developed by Kohler et al. (1975) Nature 256:495–497), as well as the trioma technique, the human B-cell hybridoma technique (Kozbor et al. (1983) Immunology Today 4:72), and the EBV-hybridoma technique to produce human monoclonal antibodies (Cole et al. (1985) in "Monoclonal Antibodies and Cancer Therapy", Alan R. Liss, Inc. pp. 77–96) and the like are within the scope of the present invention. The monoclonal antibodies for diagnostic or therapeutic use may be human monoclonal antibodies or chimeric human-mouse (or other species) monoclonal antibodies. Human monoclonal antibodies may be made by any of numerous techniques known in the art. Chimeric antibody molecules may be prepared containing a mouse antigen-binding domain with human constant regions (e.g., Takeda et al. (1985) Nature 314:452).

The present invention provides for antibody molecules as well as fragments of such antibody molecules. Antibody fragments which contain the idiotype of the molecule can be generated by known techniques. For example, such fragments include, but are not limited to, the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques including, but not limited to, immunoabsorption or immunoaffinity chromatography, chromatographic methods such as HPLC (high performance liquid chromatography), or a combination thereof.

The invention also provides for single chain Fvs. A single chain Fv (scFv) is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907, the specifications of which are herein incorporated by reference herein.

MINC102 Antagonists

In addition to antibodies specific to MINC102, the invention encompasses antagonists of MINC102, including both direct inhibitors capable of inhibiting MINC102 activity, as well as indirect inhibitors capable of inhibiting the MINC102 pathway. Antagonists include agents capable of activating the Akt pathway, thus blocking up-regulation of MINC102. Such agents include, but are not limited to, insulin-like growth factor 1 (IGF-1) and clenbuterol.

Inhibitory Nucleic Acids

In addition to agents capable of inhibiting MINC102 activity, the methods of the invention encompass inhibition of MINC102 expression with nucleic acid molecules capable of interfering with or silencing MINC102 gene expression. In one embodiment, MINC102 expression is inhibited by MINC102 antisense nucleic acid comprises at least 6 to 200 nucleotides that are antisense to a gene or cDNA encoding MINC102 or a portion thereof. As used herein, a MINC102 "antisense" nucleic acid refers to a nucleic acid capable of hybridizing by virtue of some sequence complementarity to a portion of an RNA (preferably mRNA) encoding MINC102. The antisense nucleic acid may be complementary to a coding and/or noncoding region of an mRNA encoding MINC102. The oligonucleotides can be DNA or RNA or chimeric mixtures or derivatives or modified versions thereof, can be single- or double-stranded, and can be modified at the base moiety, sugar moiety, or phosphate backbone. The oligonucleotide may include other appended groups such as peptides; agents that facilitate transport across the cell membrane (see, e.g., Letsinger et al. (1989) Proc. Natl. Acad. Sci. USA 86:6553–6556) or blood-brain barrier (see, e.g WO 89/10134,). Such antisense nucleic acids have utility as compounds that inhibit MINC102 expression, and can be used in the treatment of obesity.

In another embodiment, MINC102 may be inhibited with ribozymes or triple helix molecules which decrease MINC102 gene expression. Ribozyme molecules designed to catalytically cleave gene mRNA transcripts encoding MINC102 can be used to prevent translation of MINC102 mRNA and, therefore, expression of the gene product. (See, e.g., PCT International Publication WO90/11364). Alternatively, the endogenous expression of MINC102 can be reduced by targeting deoxyribonucleotide sequences complementary to the regulatory region of the gene (i.e., the gene promoter and/or enhancers) to form triple helical structures that prevent transcription of MINC102 in target cells in the body (see, for example, Helene et al. (1992) Ann. N.Y. Acad. Sci., 660, 27–36).

In another embodiment, MINC102 is inhibited by a short interfering RNA (siRNA) through RNA interference (RNAi) or post-transcriptional gene silencing (PTGS) (see, for example, Ketting et al. (2001) Genes Develop. 15:2654–2659). siRNA molecules can target homologous mRNA molecules for destruction by cleaving the mRNA molecule within the region spanned by the siRNA molecule. Accordingly, siRNAs capable of targeting and cleaving homologous MINC102 mRNA are useful for treating muscle atrophy.

Diagnostic Assays

The compositions of the instant invention may be used diagnostically as well as prognostically. For example, a MINC102 antibody may be used to detect the presence of MINC102 in a biological sample in order to quantitate MINC102 levels or to determine if a subject has elevated MINC102 levels. Further, a MINC102 antibody of the invention can be used to monitor levels of MINC102 in a biological sample obtained from a subject. In one embodiment, the invention includes a method of detecting muscle atrophy in an animal comprising measuring MINC102 in a patient sample.

The invention also provides for nucleic acid probes capable of hybridizing with a MINC102 nucleic acid sequence useful for the detection of MINC102 mRNA-expressing tissue in humans and rodents. Such assays are useful, for example, in determining the extent, progression, or development of muscle atrophy and/or conditions results in muscle atrophy.

In a specific embodiment, the invention provides for a method of detecting muscle atrophy in a mammal comprising a) administering to the mammal a composition which comprises a molecule capable of detecting MINC102 nucleic acid or polypeptide coupled to an imaging agent; b) allowing the composition to accumulate in the muscle; and c) detecting the accumulated composition so as to detect the presence of MINC102 as an indication of muscle atrophy.

Combination Therapies

In numerous embodiments, the therapeutic agents of the method of the invention may be administered in combination with one or more additional compounds or therapies. For example, an agent capable of inhibiting MINC102 expression can be co-administered in conjunction with one or more therapeutic compounds.

Methods of Administration

The invention provides methods of treatment comprising administering to a subject an effective amount of an agent capable of inhibiting the expression or activity of MINC102. In a preferred aspect, the agent is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

Pharmaceutical Compositions

The present invention also provides pharmaceutical compositions comprising an agent of the invention, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The agent of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes a transgenic knock-out animal having a modified endogenous MINC102 gene. A transgenic animal can be produced by introducing nucleic acid into the male pronuclei of a fertilized oocyte, e.g., by microinjection, retroviral infection, and allowing the oocyte to develop in a pseudopregnant female foster animal. Still further, the invention contemplates a transgenic animal having an exogenous MINC102 gene generated by introduction of any MINC102-encoding nucleotide sequence that can be introduced as a transgene into the genome of a non-human animal. Any of the regulatory or other sequences useful in expression vectors can form part of the transgenic sequence. A tissue-specific regulatory sequence(s) can be operably linked to the transgene to direct expression of the MINC102 protein to particular cells.

Specific Embodiments

Both in vitro and in vivo models of skeletal muscle atrophy were used to verify that the expression of a novel protein, termed MINC102, is significantly increased in atrophic conditions. Example 1 provides an example of one animal model of atrophy. Example 2 summarizes the results of experiments conducted with an in vitro model of skeletal muscle biology which utilizes the muscle cell line C2C12. These C2C12 cells can be differentiated into multi-nuclear structures called myotubes which have been characterized and shown to function in a similar way as newly-formed skeletal muscle fibers. When contacted with the cachectic glucocorticoid, dexamethasone, C2C12 myotubes undergo atrophy, e.g., their diameters decrease, and they express the atrophy-markers MuRF1 and MAFbx. MINC102 expression was increased 10–100 fold during muscle atrophy, a result confirmed in vivo (Example 3).

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Animal Model for Atrophy

To test for muscle atrophy, the ankle joint of rodents (mice or rats) are immobilized at 90 degrees of flexion. This procedure induces atrophy of the muscles with action at the ankle joint (e.g. soleus, medial and lateral gastrocnemius, tibilias anterior) to varying degrees. A reproducible amount of atrophy can be measured in hindlimb muscles over a 14-day period.

The immobilization procedure may involve either casting (mice) or pinning the ankle joint (rats). Rodents are anesthetized with ketamine/xylazine and the right ankle joint is immobilized. In rats, a 0.5 cm incision is made along the axis of the foot, over the heel region. A threaded screw (1.2×8 mm) is then inserted through the calcaneous and talis, into the shaft of the tibia. The wound is closed with skin glue. In mice, the ankle joint is fixed at 90 degrees with a light weight casting material (VET-LITE) around the joint. The material is soaked in water and then wrapped around the limb. When the material dries it is hard, but light in weight.

At seven and 14 days following the immobilization, animals are anesthetized and killed by cervical dislocation. The tibialis anterior (TA), medial gastrocnemius (MG), and soleus (Sol) muscles are removed from the right (immobilized) and left (intact) hindlimbs, weighed, and frozen at a fixed length in liquid nitrogen cooled isopentane. A cohort of control animals which are the same weight and age as the experimental animals are also killed and the muscles removed, weighed and frozen. The amount of atrophy is assessed by comparing the weight of the muscles from the immobilized limb with the weight of the muscles from the control animals. Further assessment of atrophy will be done by measuring muscle fiber size and muscle tension output.

Example 2

MINC102 Expression is Stimulated by Skeletal Myotube Atrophy In Vitro

In vitro experiments were conducted with C2C12 as previously described (see, for example, Rommel et al. (1999) Science 286:1738–1741, herein specifically incorporated by reference in its entirety). Cells contacted with the cachectic glucocorticoid, dexamethasone underwent atrophy, e.g., their diameters decreased, and they express the atrophy-markers MuRF1 and MAFbx. In addition to upregulating MuRF1 and MAFbx expression, MINC102 expression was increased 10–100 fold, as measured by Northern blot analysis. These results demonstrate that MINC102 is a marker of skeletal muscle atrophy.

Example 3

MINC102 Expression is Stimulated by Skeletal Muscle Atrophy In Vivo

Mice subjected to several models of skeletal muscle atrophy (Bodine et al. (2001) Science 294:1704–1708, herein specifically incorporated by reference in its entirety) including denervation, in which the sciatic nerve is severed causing disuse and atrophy of the affected muscles; immobilization, in which a cast is placed on the limb to immobilize it; hind-limb suspension, in which the limb is suspended such that it cannot push against a force; dexamethasone treatment, in which the animal is treated with the cachectic glucocorticoid dexamethasone at concentrations sufficient to causes skeletal muscle atrophy. Northern mRNA hybridization analysis demonstrated that MINC102 expression was increased 10–100 fold in every model examined.

What is claimed:

1. An isolated nucleic acid molecule having a sequence selected from the group consisting of:
(a) SEQ ID NO:1;
(b) a nucleotide sequence that hybridizes under stringent conditions to the complement of the nucleotide sequence of (a) and which encodes the polypeptide of SEQ ID NO: 2, wherein the stringent conditions are 30% formamide in 5×SSPE (0.18 M NaCl, 0.01 M NaPO$_4$, PH 7.7, 0.001 M EDTA) buffer at a temperature of 42° C. and remaining bound when subject to washing at 42° C. with 0.2×SSPE; or
(c) a nucleotide sequence which, as a result of the degeneracy of the genetic code, differs from the nucleic acid of (a) or (b) and which encodes the polypeptide of SEQ ID NO: 2.

2. An isolated nucleic acid sequence encoding a mouse MINC102 polypeptide, comprising:
(a) SEQ ID NO: 3; or
(b) a nucleotide sequence which, but for the degeneracy of the genetic code, would hybridize to the complement of SEQ ID NO: 3, and which encodes a protein that binds agents capable of activating the Akt pathway.

* * * * *